United States Patent [19]

Chen et al.

[11] Patent Number: 4,873,186

[45] Date of Patent: Oct. 10, 1989

[54] CORNEA STORAGE MEDIUM

[75] Inventors: Chung-Ho Chen; Sumi C. Chen, both of Phoenix, Md.

[73] Assignee: The Johns Hopkins University, Baltimore, Md.

[21] Appl. No.: 92,321

[22] Filed: Sep. 2, 1987

[51] Int. Cl.$^4$ .............................................. A01N 1/02
[52] U.S. Cl. ......................................................... 435/1
[58] Field of Search ............................................ 435/1

[56] References Cited

U.S. PATENT DOCUMENTS 4,663,289  5/1987  Veech ..................................... 435/1
4,695,536  9/1987  Lindstrom et al. ...................... 435/1

OTHER PUBLICATIONS

Messmer et al.–Chem. Abst., vol. 86 (1977), p. 151, 059c.
Sheu et al.–Chem. Abst., vol. 83 (1975), p. 173, 227w.
Bassenge et al., *Am. J. Physiol.*, 208:162 (1965).
Krebs, H. A., (1972), *The Pasteur Effect Essays Biochem.*, 8:2–34.
Williamson, *Biochem. Soc. Transactions*, 7:1313–1321 (1979).
Lindstrom et al., *Dev. Ophthal.*, 11:37–43 (1985).
Lindstrom et al., *American Journal of Ophthamology*, vol. 82, No. 1, pp. 72–82 (Jul. 1976).
Lindstrom et al., *Arch. Ophthalmol.*, 95:869–878 (May, 1977).
Veech et al., *Biochem. J.*, 115:609–619 (1969).
Veech et al., *J. of Biological Chem.*, vol. 254, No. 14, pp. 6538–6547 (Jul. 25, 1979).
Veech et al., Febs Letters, vol. 117, Supplement, Aug. 25, 1980, K65–72 (Elsevier/North–Holland Biomedical Press).
McCarey et al., *Investigative Ophthamology*, pp. 165–173 (Mar. 1974).

*Primary Examiner*—Sam Rosen
*Attorney, Agent, or Firm*—Cushman, Darby & Cushman

[57] ABSTRACT

A storage medium for isolated donor corneas comprising at least one compound capable of inhibiting corneal lactate production. The addition of a short chain fatty acid and/or a ketone body and precursors provides isolated corneas with an efficient fuel source and concurrently inhibits corneal lactate formation.

6 Claims, 1 Drawing Sheet

CORNEA STORAGE MEDIUM

BACKGROUND OF THE INVENTION

1. Technical Field

The present invention relates in general, to a storage medium for isolated donor corneas and, in particular, to a corneal storage medium which extends the period of time surgical-quality corneas may be stored.

2. Background Information

Penetrating kertoplasty for the restoration of sight in patients with corneal opacity is highly successful. However, the short supply of surgical-quality donor corneas means that many patients wait up to a year for available donor tissue.

The quantity of surgical-quality donor corneas is determined by a combination of two factors: (1) the length of time between the death of the donor and the preservation of the cornea, and (2) the length of time that the tissue remains stored. Presently, procurement of a donor cornea no more than twelve hours after death and storage for no more than 72 hours constitute the guidelines for the distribution of donor tissues for transplant. Donor corneas with a preservation time of up to 96 hours are used on an emergency basis. Statistics indicate that if the upper limit of death-to-preservation time were to be extended from 12 hours to 24 hours, 50% more donor corneas would be available for transplant.

Development of methods for extending the time donor corneas may be stored has significant clinical as well as marketing implications. Extending corneal preservation time increases the quantity of tissues available for transplant, provides surgeons flexibility in performing operations, improves scheduling of elective surgery, and affords more cost efficient use of operating rooms. Patients benefit from the enhanced physiological quality of corneal tissues.

The importance of corneal preservation for transplantation has been recognized for over 70 years. Early attempts involved the use of hemolyzed serum. Other methods that have been evaluated include cryo-preservation and storage in a moist chamber, in autologous serum and in tissue culture medium. The applicability an organ culture system involving repeated medium changes has also been examined.

Of the above-described storage systems, maintenance of isolated corneas in tissue culture medium is the method most widely used. Specifically, Medium 199 with 5% dextran (McCarey-Kaufman medium) is credited with offering superior preservation of corneal endothelium. Corneas maintained in McCarey-Kaufman medium are kept clear and this by the inclusion in the culture medium of dextran. The thus stored corneas, however, tend to swell extensively when placed in an aqueous or salt solution after storage. Recently, the possible substitution of dextran with chondroitin sulfate was evaluated. While beneficial effects of chondroitin sulfate for long-term corneal storage remain to be documented, it has been reported that corneas stored in the presence of chondroitin sulfate swell and become slightly hazy.

Currently, donor corneas are stored refrigerated in McCarey-Kaufman medium in tightly sealed vials. Under these preservation conditions, the metabolic activity of the cornea is reduced and, therefore, the energy output may be inadequate for the tissue to maintain its transparency and minimal biological activity. In addition, since the storage vials are tightly capped, the limited amount of oxygen in the medium gradually decreases. As the oxygen content decreases, anaerobic glycolytic activity increases resulting in an accumulation of excess lactate in the storage medium. The lactic acid concentration in the storage medium of surgical-quality corneas in about 0.50 mM and about 2.0 mM or more for donor corneas not suitable for surgery. The formation of lactate is accompanied by the formation of an equimolar concentration of H+. A resulting reduction in intracellular pH would adversely affect the corneal tissue.

SUMMARY OF THE INVENTION

It is a general object of the invention to obviate or minimize the objections to the prior art corneal preservation methods.

It is a particular object of the invention to provide a method of corneal storage wherein donor corneas maintain biological function, both metabolic and physiological, for extended periods.

It is another object of the invention to provide a corneal storage medium in which corneal production of lactic acid is suppressed.

Further objects and advantages of the present invention will be apparent from the following detailed description of the species thereof.

The foregoing objects of the invention are achieved by storing isolated donor corneas in a storage medium comprising at least one compound capable of inhibiting lactate production by the isolated cornea. Specifically, the inclusion in the culture medium of ketone bodies (including ketone body precursors such as $\beta$-hydroxybutyrate ($\beta$HBA) and ketogenic amino acids) and/or short-chain fatty acids provides isolated corneas with an efficient fuel source which concurrently inhibits lactate formation.

BRIEF DESCRIPTION OF THE DRAWINGS

Referring to the drawings.

DETAILED DESCRIPTION OF THE PREFERRED EMBODIMENT

Figure 1:
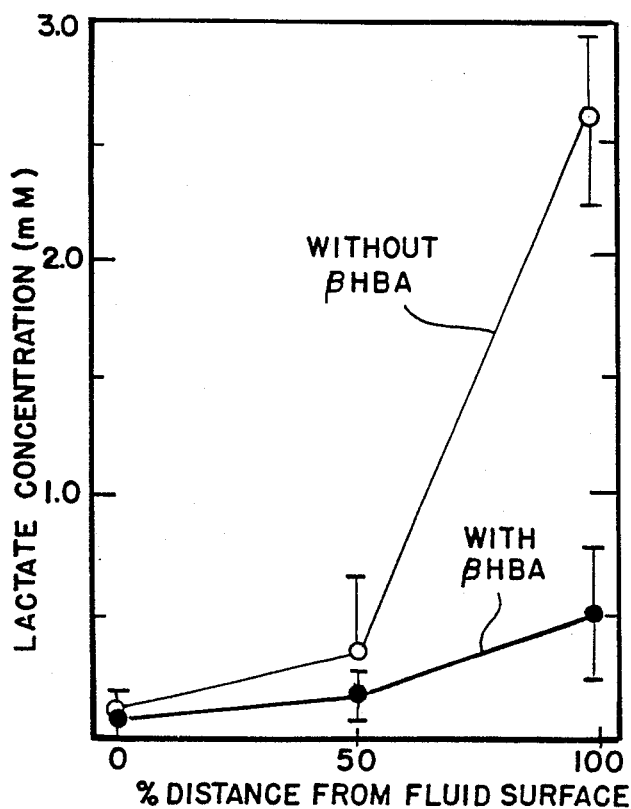
FIG. 1 illustrates the effect of $\beta$HBA on the formation of a lactic acid concentration gradient during storage.

The present invention relates to a liquid storage medium for the storage of isolated corneas comprising an amount of at least one compound capable of inhibiting the production of lactate by the isolated corneas sufficient to inhibit corneal lactate production. Isolated corneas produce lactate via anaerobic glycolysis. The invention contemplates a method of extending a time surgical quality isolated corneas can be stored comprising adding to corneal storage medium an amount of at least one compound capable of inhibiting lactate production by the isolated corneas sufficient to inhibit corneal lactate production.

The anaerobic glycolytic pathway of exogenous glucose utilization in the cornea is inhibited by the inclusion in the storage medium of short chain fatty acids and/or ketone bodies, including ketone body precursors such as $\beta$HBA and ketogenic amino acids. Acetate and butyrate are preferred short chain fatty acids because of their high solubility in the aqueous medium. Caproic acid can also be used. The use of βHBA is advantageous as it is chemically stable, cost-efficient and readily taken up and utilized by tissues. Acetoacetate can also be used. Ketogenic amino acids, including leucine, isoleucine, lysine, phenylalanine, tryptophan and typrosine, are also useful.

The invention contemplates the use of various tissue culture media as the basic storage medium. Examples of these include Medium 199 and minimum essential medium supplemented with inorganic salts such as Earle's, Dulbecco's and Hank's salts. These media are commercially available. It is preferred that bicarbonate buffer be replaced in these media with HEPES buffer (N-2-hydroxyethyl piperazine-N'-2-ethanesulfonic acid), preferably 25–40 mM. Ketogenic amino acids are present in these pre-formulated tissue culture media at concentrations of less than 1 mM. It is preferred that additional ketogenic amino acids be added to the basic storage medium to increase the concentration of each individual component, preferably to 2–5 mM. short chain fatty acids and βHBA, either individually or in combination, are added to the basic storage medium at concentrations sufficient to inhibit corneal lactate production, preferably 5–20 mM. The complete storage medium is of sufficient osmolarity, preferably 300–330 mOsM. The preferred osmolarity is achieved by varying the concentration of NaCl. It is preferred at that the pH be in the range of 7.4–7.6.

Fatty acids, βHBA and ketogenic amino acids are oxidized in the cytoplasm, yielding acetyl CoA which may accumulate in the form of ketone bodies for subsequent oxidation. The oxidation of acetyl CoA is an energy efficient process, 30 moles of ATP being formed per mole of acetyl CoA utilized. In addition, acetyl CoA oxidation enhances respiration which in turn inhibits anaerobic glycolysis via the Pasteur effect. Thus, storage media containing short chain fatty acids and/or ketone bodies and precursors both satisfies corneal nutrient requirements and. suppresses lactate formation. Isolated corneas thus stored are capable of performing energy-dependent metabolic functions, such as protein synthesis, and physiological functions such as maintaining a thin and clear tissue.

The following examples are provided for the purpose of describing the advantages of including fatty acids and/or ketone bodies and precursors in the liquid medium used in the storage of isolated corneas. It should be understood, however, that these examples are for illustrative purposes only and are by no means to be considered as limiting.

EXAMPLE 1

Freshly isolated rabbit corneas were stored at 0°–4° C. for two days in conical centrifuge tubes containing 16 ml of McCarey-Kaufman medium in the presence or absence of 20 mM βHBA. The tubes were loosely-capped to allow a free air-flow. An aliquot of 0.5 ml was carefully withdrawn from the top, midpoint, and bottom of the storage fluid in that sequence. To minimize the mixing of the medium during samplings, a capillary tubing attached to a syringe was carefully and steadily positioned inside the tube against the walls before withdrawing the medium. Lactate concentration was quantitated spectrophotometrically coupling lactate dehydrogenase and glutamate pyruvate transaminase. FIG. 1 shows that a diminishing lactate concentration gradient in corneal storage medium results from the addition of 20 mM βHBA. Data are an average of three measurements, in means ± standard deviation.

EXAMPLE 2

Figure 2:
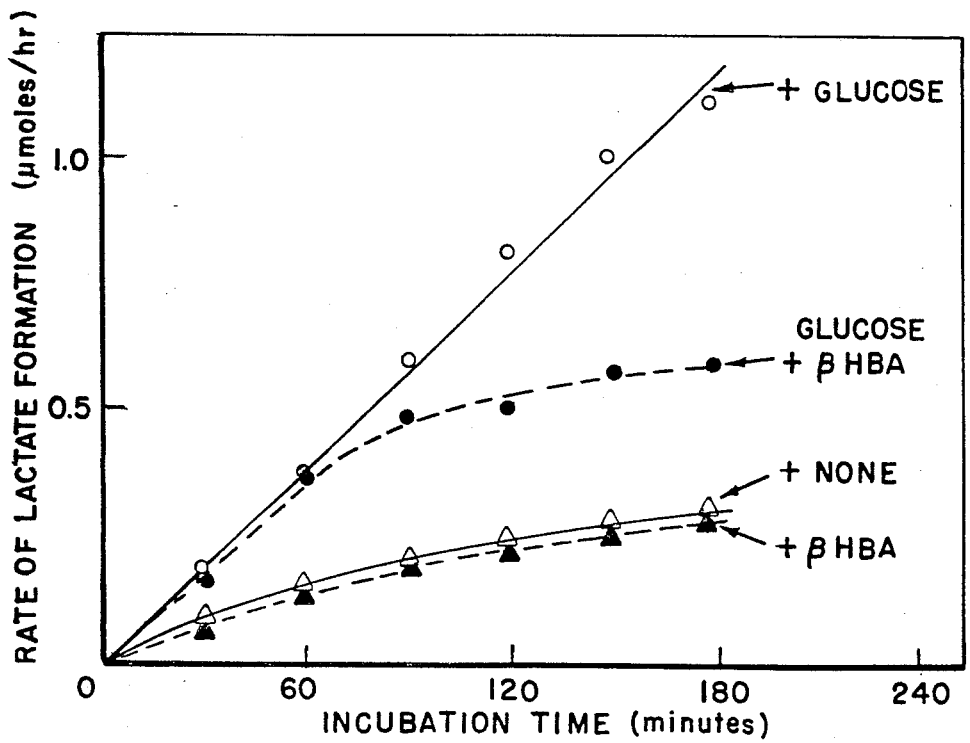
FIG. 2 illustrates the effect of $\beta$HBA on anaerobic glycolysis in isolated rabbit corneas.

Isolated rabbit corneas were rinsed by briefly dipping them into Dulbecco's phosphate buffered saline (PBS), and were then incubated in 3 ml of PBS. There was a lapse of about 35–45 min. between sacrifice of the animals and incubation of the corneas in PBS. Anaerobic glycolytic activity was measured after the isolated corneas were preincubated for 60 min. When added, glucose was 11 mM; βHBA was 10 mM. A sample volume of 500 μl was taken at indicated time intervals. Fresh medium was then added to make up the volume. The results in FIG. 2 demonstrate that in the presence of βHBA, anaerobic glycolysis is almost completely abolished following incubation for 90 min. The lag presumably results from the time required for βHBA to enter the tissue, for βHBA to be converted to acetoacetate, and for acetoacetate to be utilized by the mitochondria. Data are an average of three measurements.

EXAMPLE 3

Experimental procedures are the same as those in Example 1 except that, in addition to rabbit corneas, human donor corneas were also used; human donor ages ranged from 55 to 72 years and death-to-experiment time ranged from 9 to 15 hours. The results in Table I demonstrate that the addition of 20 mM βHBA to McCarey-Kaufman medium markedly reduces the total lactate in the corneal storage medium while resulting in the retention of a high level of glycolytic activity in both human and rabbit corneas after three days of storage. Data are an average of four experiments in means ± standard deviation.

EXAMPLE 4

In experiment I, six freshly isolated corneas from rabbits were incubated in 5 ml of Dulbecco's PBS for 90 minutes, two of the corneas were immediately frozen, extracted with PCA and adenine nucleotides quantitated. Two of the corneas were incubated with 11 mM glucose and the remaining two with 11 mM glucose and 20 mM βHBA and the samples were further incubated for 180 minutes. In experiment II the procedure was the same as that for experiment I except 20 mM βHBA alone was added. Experiments III and IV were storage experiments utilizing two corneas each. At the end of these experiments, the corneas were frozen, and extracted with PCA. Adenine nucleotides in the extracts were quantitiated and energy charges were calculated according to the method of Atkinson (Biochemistry, (1968) 7:4030). Data shown in Table II indicate that βHBA is readily utilized by isolated corneas. Corneas incubated in a medium containing βHBA for three hours at room temperature show elevated levels of ATP and energy charge. Rabbit corneas stored at 0°–4° C. in a clinical centrifuge tube containing 5 ml of McCarey-Kaufman medium for three days show markedly decreased levels of ATP and energy charge. However, moderate levels of ATP concentration and energy charge are observed when 20 mM βHBA is present. Results are an average of two measurements.

Although the foregoing invention has been described in some detail by way of examples for purposes of clarity and understanding, it will be obvious to those in the art various changes in form and detail can be made therein without departing from the true scope of the invention.

TABLE I

Effect of β-Hydroxybutyrate (βHBA) on Total Lactate Accumulation in the Medium and on Corneal Glycolytic Activity

| Corneas | Duration of Storage (days) | Volume of Medium (ml) | [βHBA] (mM) | Total Medium Lactate (μmoles) | Glycolytic Activity [per cornea] (μmoles/hr) |
|---|---|---|---|---|---|
| Humans | 0 | — | — | — | 0.87 ± 0.12 |
| | 3 | 20 | — | 12.9 ± 1.1 | 0.59 ± 0.22 |
| | 3 | 20 | 20 | 2.1 ± 0.5 | 0.75 ± 0.15 |
| Rabbits | 0 | — | — | — | 0.41 ± 0.03 |
| | 3 | 5 | — | 3.7 ± 0.7 | 0.14 ± 0.02 |
| | 3 | 5 | 20 | 0.5 ± 0.1 | 0.32 ± 0.05 |

TABLE II

Effect of Incubation Conditions on Adenine Nucleotide Concentrations and Energy Charges in Isolated Rabbit Corneas

| Exp. | Experimental Conditions | Incubation Time | [ATP] (μmoles/cornea) | [ADP] | [AMP] | Energy Charge |
|---|---|---|---|---|---|---|
| I. | In Dulbecco's PBS | 90 min | 1.95 | 0.97 | 0.95 | 0.63 |
| | "+ Glucose | 180 min | 2.25 | 0.79 | 0.72 | 0.70 |
| | "+ Glucose, βHBA | 180 min | 3.46 | 0.28 | 0.47 | 0.86 |
| II. | In PBS for 90 min, then | 180 min | 2.98 | 0.35 | 0.56 | 0.81 |
| III. | In M-K medium at 0°-4° C. | 3 days | 0.67 | 0.48 | 1.25 | 0.38 |
| IV. | In M-K medium with βHBA at 0°-4° C. | 3 days | 1.85 | 0.66 | 0.78 | 0.66 |

What is claimed is:

1. A method of extending a time a surgical quality isolated cornea can be stored which comprises including in the corneal storage medium containing the stored cornea, an amount of at least one compound selected from the group consisting of short chain fatty acids, ketone bodies and ketogenic amino acids capable of inhibiting lactate production by said isolated cornea sufficient to inhibit said lactate production.

2. A method according to claim 1 wherein said compound is a short chain fatty acid.

3. A method according to claim 1 wherein said compound is ketone body.

4. A method according to claim 1 wherein said compound is β-hydroxybutyrate.

5. A method according to claim 1 wherein said compound is a ketogenic amino acid.

6. A method of extending a time a surgical quality isolated cornea can be stored which comprises including in the corneal storage medium containing the stored cornea, an amount of at least one compound selected from the group consisting of short chain fatty acids and ketone bodies and ketone body precursors capable of inhibiting lactate production by said isolated cornea sufficient to inhibit said lactate production.

* * * * *